United States Patent [19]

Thomas

[11] 4,200,187
[45] Apr. 29, 1980

[54] LENS CASE WITH OPPOSITELY HINGED BASKETS

[75] Inventor: Michael D. Thomas, Arab, Ala.

[73] Assignee: Ryder International Corporation, Hanover Park, Ill.

[21] Appl. No.: 955,394

[22] Filed: Oct. 27, 1978

[51] Int. Cl.$^2$ .................... A45C 11/00; B08B 3/04
[52] U.S. Cl. ............................... 206/5.1; 220/288
[58] Field of Search ............. 206/5.1, 15.2; 220/288

[56] References Cited

U.S. PATENT DOCUMENTS

| | | | |
|---|---|---|---|
| 2,917,766 | 12/1959 | Ciffo | 206/15.2 |
| 3,151,740 | 10/1964 | Simon | 220/288 |
| 3,871,395 | 3/1975 | Murry | 206/5.1 |
| 4,011,941 | 3/1977 | Parsons | 206/5.1 |

*Primary Examiner*—William T. Dixson, Jr.
*Attorney, Agent, or Firm*—Trexler, Wolters, Bushnell & Fosse, Ltd.

[57] ABSTRACT

The disclosure relates to a lens case for supporting a pair of contact lenses in a liquid solution to be heated to an elevated temperature for effecting sterilization or disinfecting of the lenses. The lens case includes a generally cylindrical open ended container for housing the liquid, a cap for closing the open end of the container, and a lens holder arrangement for supporting the lenses to be sterilized. The cap includes means for supporting the lens holder and the lenses confined therein emersed within the liquid. Further, said cap includes a circumferential downturned annular flange that forms a recess within the cap to provide an air pocket and an area which provides an expansion chamber for the liquid. More specifically, upon assembly of the cap to a filled container, the air pocket will displace excess liquid from the container as the cap is assembled in place. Thus, the liquid level in the container is controlled with the area or air pocket therefore providing an expansion chamber for liquid vapors produced during heating. Further, the lens holder is of unique design in that it includes a central body having a pair of laterally and oppositely facing convex surfaces, and a like pair of covers having a concave inner surface corresponding to the convex surfaces of the central body. The covers are releasably and oppositely hinged with respect to the central body by resilient hinge members which releasably attach to the side edges of the central body for providing lateral opening and closing movement of the covers with respect to the central body. Said covers cooperate with the convex surface for confining a pair of contact lenses therebetween.

10 Claims, 5 Drawing Figures

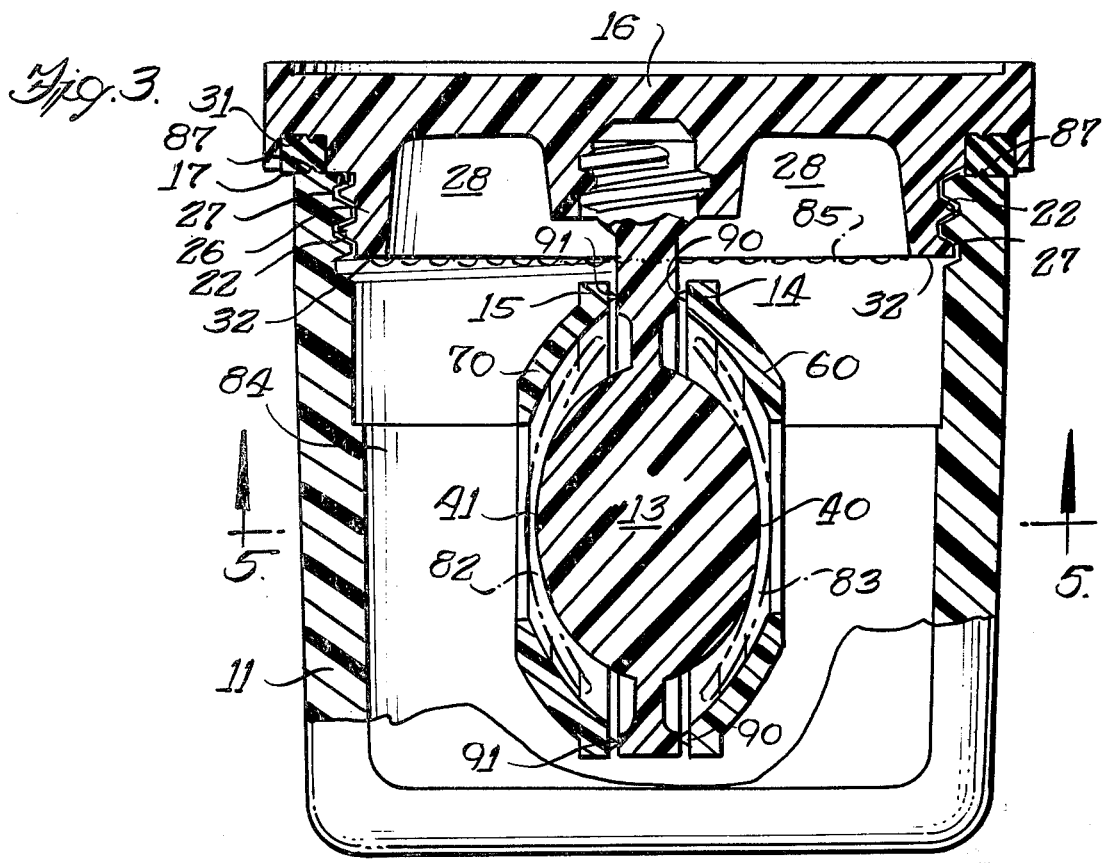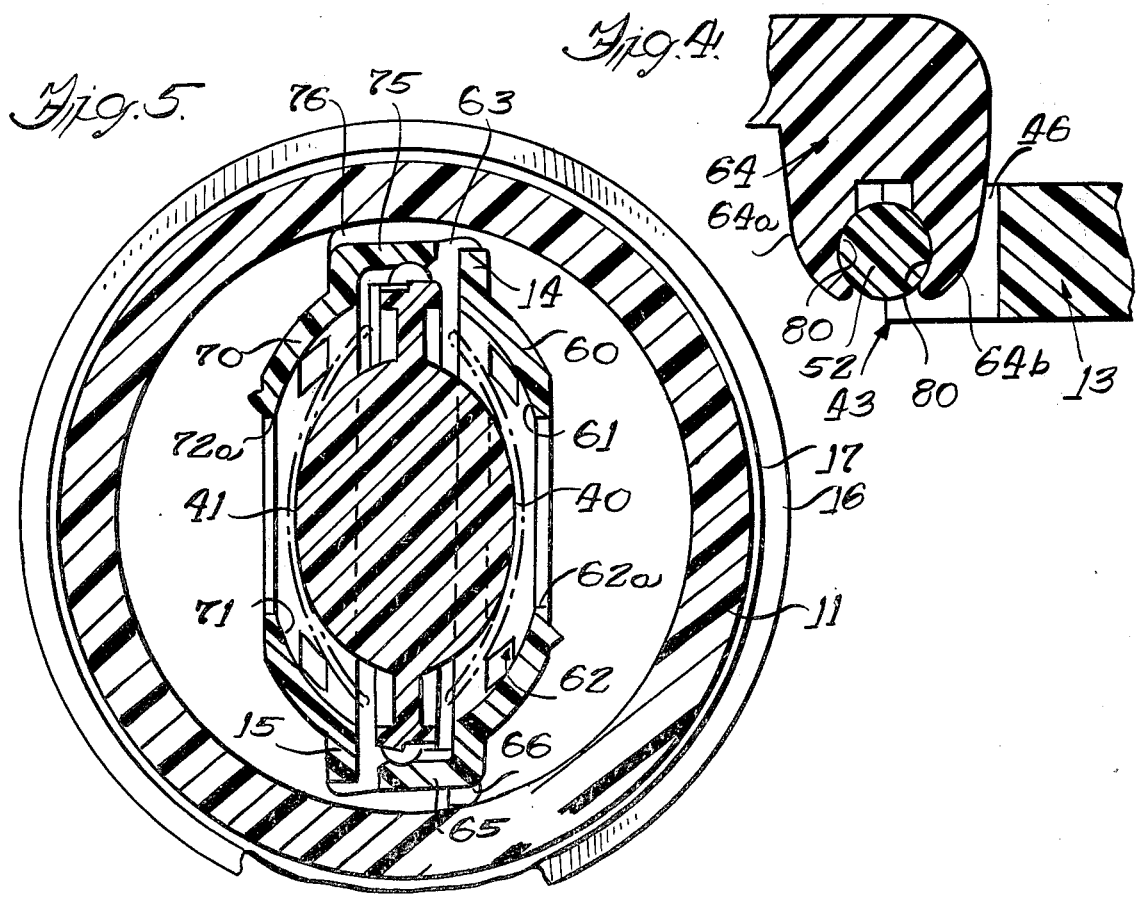

LENS CASE WITH OPPOSITELY HINGED BASKETS

BACKGROUND OF THE INVENTION

The present invention generally relates to contact lens cases and more particularly to contact lens cases which are utilized in the disinfecting or sterilizing of a pair of contact lenses.

While it is desirable to disinfect all contact lenses, those of the soft type must be sterilized or disinfected, periodically to prevent eye infections. Further, the large numbers of different lens prescriptions often encountered by doctors and manufacturers require the individual pairs of contact lenses to be maintained separate. To this end, each pair of lenses is normally housed or stored in a separate container, which container or case also has separate receptacles therein for holding the right and left lenses. These containers are commonly referred to as lens cases, and most particularly in the case of soft lenses, serve both as a disinfecting vessel as well as a carrying case for the lenses.

During disinfecting or sterilizing procedure, a quantity of liquid solution is placed in the container and the lenses emersed therein. The container and the sterilizing or disinfecting solution is then heated to a desired temperature. The liquid solution within the container is in direct contact with the lenses and effects sterilization or disinfecting thereof. After the desired temperature has been reached, the lens case is removed from the heating apparatus and allowed to cool sufficiently to enable removal of the contact lenses holders and the lenses themselves. One common type of contact lens case which has gained wide acceptance in the disinfecting or sterilization of contact lenses is shown in U.S. Pat. No. 3,770,113, issued to the present inventor.

While the prior design is satisfactory for many uses, in those instances where it is desired or necessary to superheat the sterilizing solution, that is heat it above its boiling point, the case must provide a substantially air tight seal at least up to the desired temperature. One problem presently encountered is that the increased pressures encountered during superheating cannot be accommodated by existing case designs. This problem is further magnified should the lens case be over-filled with sterilizing solution, which produces increased vapor pressure resulting from the fact that as the liquid solution vaporizes, and, there exists no space to accommodate said vapor, thus tending to accelerate the pressure increase within the case. Furthermore, many of the lens holders utilized in the prior art have proved rather cumbersome in use, in that the manner in which the covers open makes it difficult for the user to placed the contact lenses into the holders without inadvertent dropping of the lenses.

Lastly, the contact lens cases of the prior art have not been easy to clean due to the fact that they cannot be taken apart. For example, the lens holders have not been removable from the container cap and the covers for the contact lenses have not been removable from the lens holders.

It is therefore a general object of the present invention to provide a new and improved lens case for use in the sterilization of contact lenses.

It is a further object of the present invention to provide a new and improved contact lens case which protects against overfilling of the lens case with the sterilization solution, insuring that an adequate volume remains in the lens case to accommodate expansion of the fluid as it is heated to the sterilization temperature and to contain the fluid vapor pressure so as to maintain the sealed integrity of the lens case during the sterilization of the contact lens.

It is a still more specific object of the present invention to provide a lens case wherein the component parts thereof may be disassembled to facilitate convenient cleaning.

The invention therefore provides a lens case for supporting a pair of contact lenses in a sterilizing solution for heating to an elevated temperature, to effect sterilization or disinfecting of the lenses. Initially, the holding or storage means for the lenses is of a novel design, employing oppositely, laterally hinged covers, which facilitate use of the holder. The lens case design, further comprises a generally cylindrical container for the sterilizing solution and having an open end, a cap or cover for closing said open end, and lens holding means mounted to said cover and arranged to confine the lenses to be sterilized. The cap or cover includes means for supporting the lens holding means and the lenses confined therein within the sterilizing solution, and includes an annular downwardly extending flange. The said flange serves to define a recess within the cap and thus provides an area or expansion chamber for accommodating the liquid vapor produced upon heating. As a further matter, the flange also provides an air pocket which will upon assembly of the cap to a filled container displace excess liquid from the container to limit the amount of liquid which remains in the container upon mounting of the cap and emersion of the lens holding means within the sterilizing solution.

BRIEF DESCRIPTION OF THE DRAWINGS

The features of the present invention which are believed to be novel are set forth with particularly in the appended claims. The objects and other advantages thereof may best be understood by making reference to the following description taken in conjunction with the accompanying drawings, wherein in the several figures of which like reference numerals identify like elements, and wherein:

FIG. 3 is a cross-sectional view of the lens case of FIG. 1 in its fully assembled condition and supporting a pair of contact lenses within a liquid prior to sterilization thereof;

FIG. 4 is a cross-sectional view taken along lines 4—4 of FIG. 2; and

FIG. 5 is a cross-sectional view taken along lines 5—5 of FIG. 3.

DESCRIPTION OF THE PREFERRED EMBODIMENT

Figure 1:
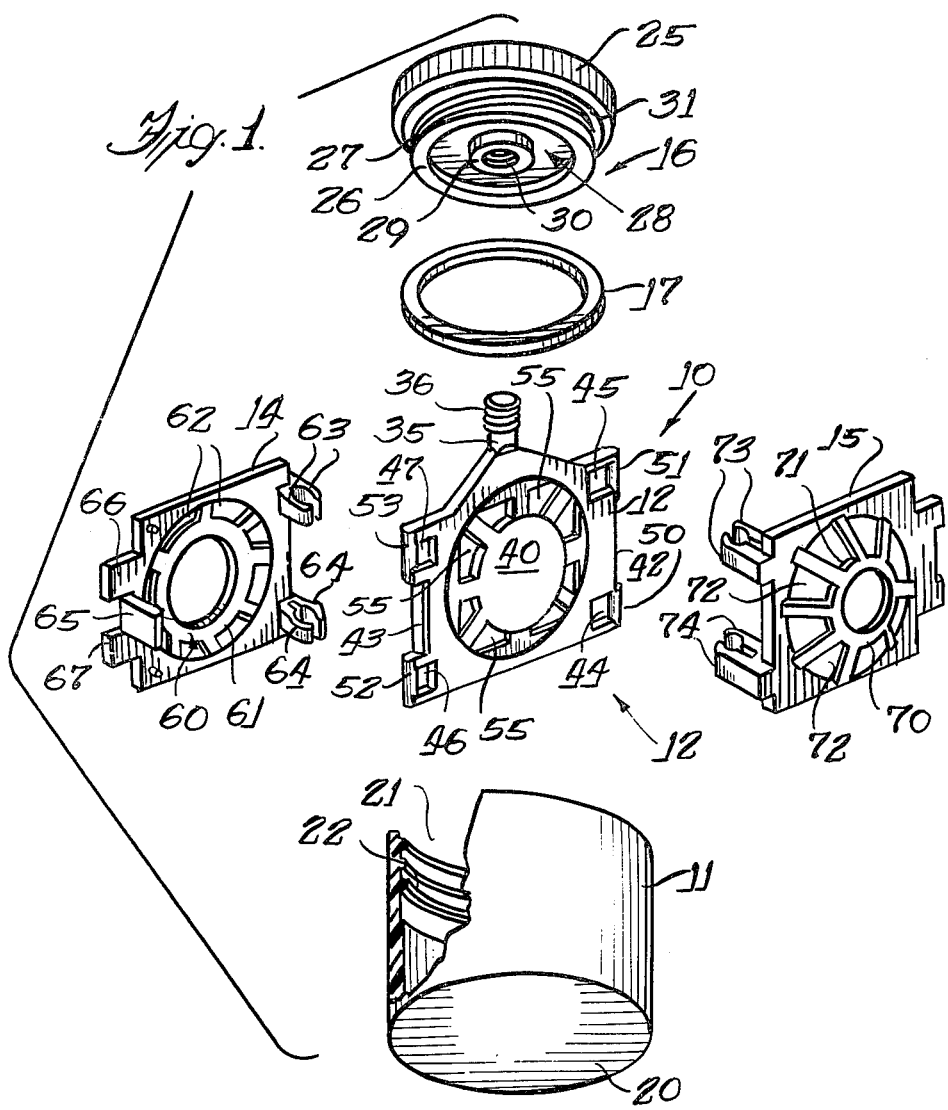
FIG. 1 is an exploded, perspective view of a lens case embodying the present invention.

FIG. 1 is an exploded perspective view of a lens case embodying the present invention and designated generally 10. The lens case 10 includes a cylindrical container 11, a lens holding means 12 comprised of a central body 13 and a pair of oppositely hinged, covers 14 and 15, a cap or cover 16, and a sealing gasket 17.

The container 11 is generally cylindrical in configuration, and includes a closed end defined by a bottom 20 and an open end 21. The container 11, when the lens case is utilized for sterilizing a pair of contact lenses, is in direct or indirect contact with a heating medium and serves to transmit heat directly from the heating medium to the sterilizing solution within the container 11, to effect the sterilization or disinfecting of the contact lenses. In the illustrated form of the invention, there is provided, about the periphery of the container at its open end 21, an internal thread 22 which, as will be more fully described hereinafter, is utilized for mounting of the cap or cover 16 to the container 11.

The cap 16 of the illustrated embodiment is of a unique design and includes a lid portion 25 which is of a greater diameter than the diameter of the container 11, disposed inwardly of the outer circumferential surface of cap 25 there is provided a downturned or downwardly extending, annular flange 26 which has an external thread 27 which is arranged to mate with the internal thread 22 of the container. The downwardly extending flange 26 forms a recess 28 within the cap 16 which functions in a manner to be described hereinafter. A boss 29 is provided within the recess 28 and centrally located with respect to the diameter dimension of the cap 16, and includes an internal thread 30 for mounting of the lens holding means 12 to said cap. Between the maximum diameter dimension of the cap formed by the lid portion 25 and the flange 26 there is provided an annular recess 31, dimensioned for receiving and retaining the sealing gasket 17.

Attention is now directed to the lens holder 12 which, as previously mentioned, includes the central body 13 and the cover members 14 and 15. The central body 13 has an extension 35 having an external thread 36 thereon. The external thread 36 is arranged to mate with the internal thread 30 of the boss 29 so that the lens holder 12 may be releasably secured to the cap 16. The central body 13 also includes a pair of oppositely and laterally facing convex surfaces 40 and 41 (FIG. 3) and a pair of vertical side edges 42 and 43. Closely adjacent each side edge 42 and 43 are a pair of slots, slots 44 and 45 being adjacent to side edge 42 and slots 46 and 47 being adjacent to side edge 43. The slots 44-47 serve to define pin means 50, 51, 52 and 53, respectively. The central body 13 also includes a plurality of openings 56 spaced around the convex surfaces 40 and 41 which promote the flow of sterilization liquid about the contact lenses during the sterilization operation.

The covers 14 and 15 are of substantially identical configuration, as such cover 14 will be discussed in detail, it being understood that cover 15 includes corresponding structural features. Cover 14 has a basket-like central portion 60 which defines a generally concave inner surface 61 corresponding to the convex external surface 40 of the central body 13. The basket-like structure 60 is of a web-like matrix or design and includes a plurality of openings 62 disposed about a central opening 62a. The cover 14 also includes two pairs of resilient, bifurcated projections or fingers 63 and 64 which serve to form releasable hinge means for the cover. More specifically, the projections 63 and 64 are arranged to be engaged releasably over the pins 53 and 52, respectively, to provide a detachale hinge connection between the cover 14 and central body 13 and to provide for the lateral opening and closing of the cover 14 with respect to the body 13.

On the side edge of the cover 14 opposite the projections 63 and 64 there is provided a releasable latch extension 65. The latch 65 is arranged to engage the side edge 42 of the central body 13 with a snap-fit for releasably locking the cover 14 to the central body 13 in a closed position. Lastly, a pair of lateral projections 66 and 67 are provided adjacent the latch 65, and which extend beyond the side edge 42 of the central body 13 when the cover 14 is in a closed position to provide tab means to facilitate grasping and opening of the cover 14.

In a similar manner, cover 15 includes a basket-like central portion 70 which is of a web-like design and also defines a concave inner surface 71 generally corresponding to the convex surface 41 of the central body 13. The cover 15 also includes a like plurality of opening 72 which are disposed about a central opening 72a. Two pairs of bifurcated projections 73 and 74 also extend from one side edge of the cover 15 to releasably receive or latch onto the pins 50 and 51, respectively, of the main section 13. Hence, the cover 15 is also provided with a releasable hinge of identical construction to that provided cover 14. For locking cover 15 in a closed position to the central body 13, the cover 15 is also provided, at the side edge opposite the projections 73 and 74, with a resilient latch 75 which latches to the side wall 43 of the central body 13 as shown in FIG. 5.

Figure 2:
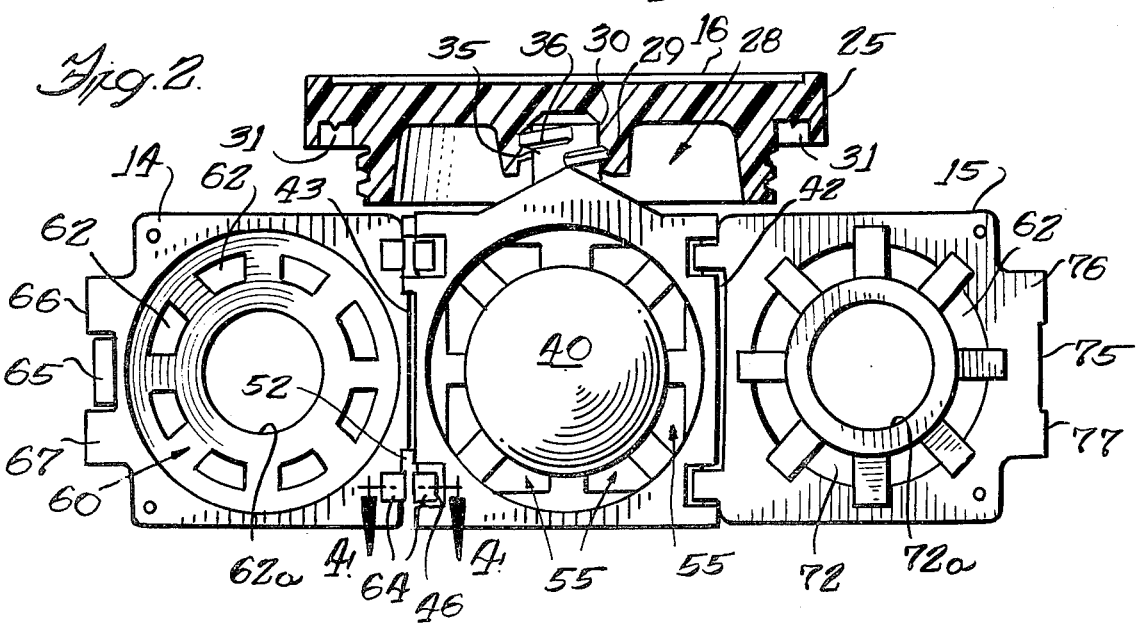
FIG. 2 is a side view, partially in cross-section, showing the lens case cap and lens holder assembled together with the lens holder covers being open.

Referring now to FIG. 2, the covers 14 and 15 as shown hingedly mounted to the central body 13 and in an open position with the central body being releasably secured to the cap 16 by the engagement of the external threads 36 on extension 35 with the internal threads 30 of boss 29. Clearly seen in FIG. 2 is the circumferential recess 31 for reception of the sealing gasket 17.

A detailed illustration of the releasable lock between one pair of projections 64 with its corresponding pin 52 of central body 13 is shown in FIG. 4. There it may be seen that the bifurcated projection 64 has a pair of spaced resilient arms 64a and 64b, which serve to define inner surface portions 80 which are arcuate for confining engagement with the pin 52 on the main body 13. As a result of the resiliency of arms 64a and 64b, the covers 14 and 15 may be easily engaged with, or removed from the central body 13 to facilitate assembly and/or cleaning. Furthermore, because the central body is threadingly received by the cap, it is therefore releasably mounted to the cap to facilitate disassembly therefrom for convenient cleaning.

As mentioned previously, the annular flange 26 serves to define a recess or chamber 28 within the cap. The chamber 28 serves two important functions, initially upon filling and assembly of cap 16 it functions as an air trap to protect against overfilling of the container, and secondly, once assembled the chamber 28 provides an expansion chamber for liquid and liquid vapor which allows the sterilizing liquid to be heated above it boiling point, as will be explained. The function of the chamber 28 as an expansion chamber will be considered first, as it is believed beneficial to first appreciate the necessity for the provision of a liquid free expansion chamber, before considering the manner by which the design of the present invention assures attainment thereof.

Accordingly, with reference to FIG. 3, there is illustrated a preferred design of lens case of the present invention in its fully assembled condition. In this regard, the lens holder 12 is shown supporting a pair of contact lenses 82 and 83 within a liquid or fluid medium 84 which has been introduced into the container 11 to facilitate sterilization of the contact lenses. The cover 16 is mounted in position with the inner peripheral thread 22 of the container engaged with the external thread 27 of the downturned annular flange 26, which threaded engagement is sufficient to hold the cover in place, but for a purpose to be discussed it is of a loose engagement as shown in FIG. 3. In order to obtain the final seal, the sealing gasket 17 is engaged with the end face of the open end 21 of container 11, which end face may include an annular bead or protuberance 87 to enhance the seal.

It should be noted that the upper level of the liquid 84 does not exceed a datum line 85 defined essentially by the lower extremity of the flange 26. As such, the chamber 28 provided by said flange is not filled with the liquid medium 84. During sterilization or disinfecting of the lenses 82 and 83, it must be kept in mind that heating of said liquid 84 is to be to a level (250° F. for example) which is in excess of the normal, atmospheric boiling temperature of said liquid 84. As the temperature of the liquid 84 approaches the boiling point, the liquid will expand and also liquid vapor will be produced, with the chamber 28 serving to accommodate said expansion and vapor. Since the vessel or container 11 is sealed via cap 16 and seal 17, the internal pressure will increase, permitting the liquid 84 to be heated to level above its normal or atmospheric boiling temperature, which is often required to effect the desired disinfecting of the lenses.

It can be appreciated that the air or vapor tight nature of the seal provided by gasket 17 is such that it can withstand only limited, internal pressure before it "blows out". By insuring the presence of a liquid free expansion chamber 28, the lens case 10 can be designed so that the desired disinfecting temperature is reached long before the seal 17 fails. More specifically, the presence of the expansion chamber 28 filled with air at atmospheric pressure, will accommodate a degree of liquid expansion and liquid vapor, before the internal pressure builds to a critical level with respect to the seal 17. If the chamber 28 were not provided, or if the area 28 were filled with the liquid 84, the pressure build up within the vessel 11 would be rapid once the atmospheric boiling temperature was reached, and the internal pressure might exceed the limits of seal 17 before the disinfecting temperature was attained.

The manner by which the lens case 10 of the present invention serves to insure the provision of a liquid free expansion chamber 28 will now be considered. In this regard, the primary danger results from over-filling of the vessel or container 11. For purposes of discussion it will be assumed that the vessel 11 is initially filled to its uppermost level as defined by the open end 21. As the lens holder portion 12 is emersed in the liquid 84, prior to engagement of the threads 26 and 27, a volume of liquid will be displaced flowing over the edge of open end 21. Assuming now that the threads 26 and 27 are in initial engagement, that is with the seal 17 spaced well above the end 21, rotation of the cap 16 will produce further emersion of the holder 12 in the liquid 84, and also commence to dispose flange 26 and the air pocket of chamber 28 inwardly of the open end 21. Due to the relatively loose fit between the threads 26 and 27 the liquid displaced by the flange 26 and the air pocket afforded by chamber 28 may still escape the vessel 11, passing upwardly between the thread surfaces and over the edge of open end 21. Thus, it is only when the seal 17 is brought into engagement, is the expelling of liquid 84 from vessel 11 precluded.

From the foregoing, it can be clearly seen that the present invention provides a new and improved lens case for supporting a pair of contact lenses in a liquid, which upon being heated to an elevated temperature, effects sterilization of the lenses. Not only are the covers arranged to open and close laterally with respect to the central body of the lens holder to facilitate convenient placing of the contact lenses therein, but also, are detachable from the central body to provide convenient cleaning. Furthermore, the central body is detachable from the cap so that it and the cap may be easily cleaned as well. In addition, by virtue of the provision of chamber 28 in the cap 16 and the air pocket formed thereby during assembly of the cap 16 to vessel 11, excess liquid will be exhausted or expelled from the container or vessel 11, as the cap is engaged. Further, the existence of the chamber 28 also provides an expansion chamber which permits the liquid to be heated above the normal boiling temperature of the liquid, without danger of failure of the seal.

While a specific, preferred embodiment of the present invention is shown and described, it is contemplated that modifications may be made, by those skilled in the art, and possessed of this disclosure, it is therefore intended that the appended claims cover all such changes and modifications which fall within the true spirit and scope of the invention, as defined by said claims.

The invention is claimed as follows:

1. A lens case for supporting a pair of contact lenses in a disinfecting liquid solution, which upon being heated to an elevated temperature, effects sterilization or disinfecting of the lenses, said lens case comprising: a generally cylindrical container for the liquid and having an internal thread about its periphery at its open end; lens holding means arranged to confine the lenses to be sterilized; and a cap having a maximum diameter dimension for overlying the open end of said container, means for providing sealing engagement between said container and said cap; and means attaching said lens holding means to the cap with the lenses confined therein for disposition within the liquid; said cap further including a circumferentially downwardly extending, annular flange having an external thread on the outer surface thereof for mating with said container internal thread; said flange also forming a recess within said cap to provide an area into which the liquid may expand as it is heated for protecting said sealing engagement, and for providing an air pocket for displacing excess liquid from the container as said cap and lens holding means are assembled to said container, thereby insuring that said container is not filled above a desired level.

2. A lens case for supporting a pair of contact lenses in emersed relation with respect to a sterilizing or disinfecting solution to be heated to an elevated temperature, said lens case comprising: a generally cylindrical closed bottom container having an open end; a cap member adapted to be attached to said container to close said open end; means for sealing said open end when closed by said cap; lens holding means for receiving and supporting a pair of contact lenses for emersion in said solution; and means affixing said lens holding means to said cap member; said cap member further including downwardly extending, annular flange means for reception within the open end of said container, said annular flange means serving to define an area which, upon assembly of the cap member to the container filled with solution, will provide an air pocket that will displace excess liquid from the container as the cap member and lens holding means are assembled thereto, thereby insuring that said container is not filled above a desired level, as defined by said air pocket, with said area provided by said flange also adapted to serve as an expansion chamber for the vapor provided upon heating of said liquid solution.

3. A lens case as defined in claim 1 or 2 wherein said sealing means includes a sealing gasket carried by said cap and wherein said cap includes a circumferential lip between said circumferential flange and said maximum diameter, said lip having an under surface and a circumferential recess therein, and wherein said sealing gasket is confined within said lip recess and is arranged to make tight sealing engagement with the open end of said container when said cap is threadingly secured to said container.

4. A lens case as defined in claim 1 or 2 wherein said means attaching said lens holding means to said cap is releasable.

5. A lens case for supporting a pair of contact lenses in a disinfecting liquid solution, which upon being heated to an elevated temperature, effects sterilization or disinfecting of the lenses, said lens case comprising: a generally cylindrical open ended container for the liquid solution; lens holding means for retaining the lenses to be sterilized; and a cap for overlying the open end of said container, means for providing sealing engagement between said container and said cap; and means attaching said lens holding means to the undersurface of the cap, such that the lenses will be confined for disposition within the liquid solution; said cap further including a recess formed in the undersurface of said cap with the entire recess including the outer peripheral portion thereof being received within the open end of said container upon assembly of the cap thereto, with said recess providing a chamber into which the liquid or any liquid vapor may expand upon heating of the liquid solution, and said chamber also providing an air pocket for displacing excess liquid from the container as said cap and lens holding means are assembled to said container, thereby insuring that said container is not filled above a desired level.

6. A lens according to claim 5 wherein said recess is defined at least partially by downwardly depending flange means being received within the open-end of said container.

7. A lens case according to claim 6 wherein said means for providing sealed engagement of the cap to the container includes an internal thread formation on said container and an external thread formation on said downwardly depending flange means.

8. A lens case according to claim 7, wherein the respective thread formations are of a loose fit, such that liquid displaced by said air pocket can be dispelled from the container past the engaged thread formations.

9. A lens case according to claims 6, 7 or 8 wherein said means for providing sealed engagement includes an annular, elastomeric seal member carried by said cap.

10. A lens case as defined in claim 1 or claim 4 or claim 2 wherein said lens holding means comprises, a central body having a pair of laterally and oppositely facing convex surfaces, a pair of side edges, and a pair of cover members, each said cover member including a substantially concave inner surface corresponding generally to a respective one of said convex surfaces for loosely confining a contact lens therebetween when said cover members are in the closed position, and releasable hinge means arranged to be releasably coupled to a respective one of said edges to provide lateral, pivotal opening and closing movement of said covers with respect to said convex surfaces, and latch means on said body and cover members for latching said covers to said central body in a closed position.

* * * * *

UNITED STATES PATENT AND TRADEMARK OFFICE
CERTIFICATE OF CORRECTION

PATENT NO. : 4,200,187
DATED : April 29, 1980
INVENTOR(S) : Michael D. Thomas

It is certified that error appears in the above-identified patent and that said Letters Patent are hereby corrected as shown below:

Column 8, line 5, after "lens", insert --case--;

Column 8, lines 21-22, change "claim 1 or claim 4 or claim 2" to --claim 1 or claim 2 or claim 5--;

Column 8, line 31, after "said", insert --side--.

Signed and Sealed this

Fifth Day of August 1980

[SEAL]

Attest:

SIDNEY A. DIAMOND

Attesting Officer    Commissioner of Patents and Trademarks